United States Patent
Yamamoto et al.

(10) Patent No.: US 6,861,552 B2
(45) Date of Patent: Mar. 1, 2005

(54) ADAMANTYL ESTER MONOMER COMPOSITION

(75) Inventors: Hiromasa Yamamoto, Yamaguchi (JP); Masao Yamaguchi, Yamaguchi (JP); Yoshihiro Hirota, Yamaguchi (JP)

(73) Assignee: Tokuyama Corporation, Tokuyama (JP)

( * ) Notice: Subject to any disclaimer, the term of this patent is extended or adjusted under 35 U.S.C. 154(b) by 60 days.

(21) Appl. No.: 10/343,606

(22) PCT Filed: Jul. 18, 2001

(86) PCT No.: PCT/JP01/06207

§ 371 (c)(1),
(2), (4) Date: Feb. 3, 2003

(87) PCT Pub. No.: WO02/12163

PCT Pub. Date: Feb. 14, 2002

(65) Prior Publication Data

US 2004/0015008 A1 Jan. 22, 2004

(30) Foreign Application Priority Data

Aug. 3, 2000 (JP) ........................................ 2000-235403

(51) Int. Cl.$^7$ .............................................. C07C 69/74
(52) U.S. Cl. ...................................... 560/128; 560/205
(58) Field of Search ................................. 560/128, 205

(56) References Cited

U.S. PATENT DOCUMENTS 3,984,372 A * 10/1976 Cottman ..................... 528/125

FOREIGN PATENT DOCUMENTS

| JP | 3-115385 | 5/1991 |
| JP | 3-121188 | 5/1991 |
| JP | 3-124790 | 5/1991 |

OTHER PUBLICATIONS

International Preliminary Search Report for PCT JP01/06207.*
International Preliminary Search Report for PCT/JP01?06207.*

* cited by examiner

*Primary Examiner*—Rita Desai
*Assistant Examiner*—Hector M. Reyes
(74) *Attorney, Agent, or Firm*—Oblon, Spivak, McClelland, Maier & Neustadt, P.C.

(57) ABSTRACT

The present invention discloses an adamantyl ester monomer composition characterized by containing at least an adamantyl ester monomer having at least one polymerizable unsaturated bond in the molecule, and a compound represented by the following general formula (1):

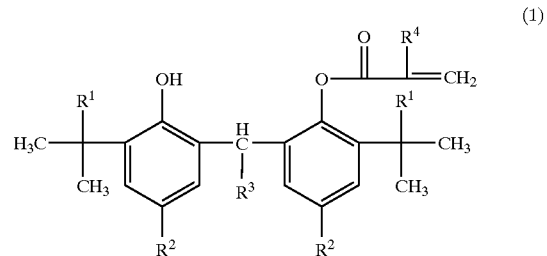

(1)

(in the formula, $R^1$ is an alkyl group of 1 to 5 carbon atoms, $R^2$ is an alkyl group of 1 to 5 carbon atoms, $R^3$ is a hydrogen atom or an alkyl group of 1 to 5 carbon atoms, and $R^4$ is a hydrogen atom or a methyl group). The composition has high storage stability and, by subjecting it to distillation, an adamantyl ester monomer of high purity can be obtained easily.

21 Claims, No Drawings

ADAMANTYL ESTER MONOMER COMPOSITION

TECHNICAL FIELD

The present invention relates to an adamantyl ester monomer composition having high storage stability, as well as to a process for producing an adamantyl ester monomer of high purity from the composition.

BACKGROUND ART

In recent years, it was reported in, for example, JP-A-5-265212 that polymers obtained from an adamantyl ester monomer have high resistance to dry etching in the process for semiconductor production. Therefore, attention is being paid to the future prospect of adamantyl ester monomer as a raw material for the resist used in semiconductor production.

The adamantyl ester monomer is generally produced by reacting an adamantane derivative (the examples thereof are shown below or the like) with a carboxylic acid compound or a derivative thereof, such as acrylic acid or methacrylic acid [hereinafter, both are referred to as (meth)acrylic acid], (meth)acrylic acid derivative or the like, to give rise to esterification.

(i) An adamantyl monool compound obtained by oxidizing adamantane or an alkyl-substituted adamantane.

(ii) An adamantyl diol compound.

(iii) A 2-alkyl-substituted-2-adamantanol compound obtained by alkylating 2-adamantanone (obtained by oxidation of adamantane) with an organometallic reagent.

Resist materials used in semiconductor production are required to have a high purity so as to be suitably used in fine processing.

Therefore, when an adamantyl ester monomer obtained by the above production process is used in a resist material for semiconductor production, the monomer need be purified in order to remove the impurities contained therein, such as metal component and the like. However, when the purification is conducted by distillation, the adamantyl ester monomer causes gelling during the distillation, which tends to incur pipe plugging and solidification in still. Therefore, it is difficult to purify the adamantyl ester monomer stably by distillation.

Thus, no method is known which can provide, from a crude adamantyl ester monomer containing impurities, an adamantyl ester monomer of high purity stably by a simple method of distillation; and development of such a method is desired.

DISCLOSURE OF THE INVENTION

In distilling a polymerizable monomer, a polymerization inhibitor is generally added to the monomer in order to prevent the polymerization of the monomer taking place during the distillation. As the polymerization inhibitor used for such a purpose, there are known phenol type polymerization inhibitors such as hydroquinone, 4-methoxyphenol and the like; quinone type polymerization inhibitors such as parabenzoquinone, 2,5-di-tert-butylbenzoquinone and the like; and aromatic amine type polymerization inhibitors such as phenothiazine and the like.

The present inventors first tried to distill an adamantyl ester monomer by adding thereto a generally used polymerization inhibitor such as mentioned above. However, since the boiling point of adamantyl ester monomer is generally high, a high distillation temperature is needed. In this case, the following problems, for example, have appeared probably owing to the high-temperature distillation. That is, the polymerization inhibitor is distilled and the amount of the polymerization inhibitor in still is decreased, which invites gelling in the still in the latter period of distillation; and the adamantyl ester monomer or the polymerization inhibitor used in distillate is decomposed, which invites coloring of the distillate.

Next, the present inventors thought that it might be possible to prevent the occurrence of the above problems by using a polymerization inhibitor having a large molecular weight. Hence, a polymerization inhibitor of large molecular weight, specifically an aromatic amine type polymerization inhibitor, i.e. N,N'-diphenyl-p-phenylenediamine or N,N'-dinaphthyl-p-phenylenediamine was added to an adamantyl ester monomer and distillation was tried. However, the stabilization effect of such a polymerization inhibitor toward adamantyl ester monomer was low and the gelling of monomer in still and the coloring of distillate could not be prevented sufficiently.

Hence, the present inventors further made studies on the stabilization effect of large molecular weight polymerization inhibitor other than those mentioned above, toward adamantyl ester monomer.

As a result, it was found out that by using a particular polymerization inhibitor, an adamantyl ester monomer could be purified stably by distillation without causing the above-mentioned problems. The finding has led to the completion of the present invention.

That is, the present invention lies in an adamantyl ester monomer composition characterized by containing at least an adamantyl ester monomer wherein a carbon atom of the adamantane skeleton is bonded with an organic residue having at least one polymerizable unsaturated bond via —OCO— bond, and a compound represented by the following general formula (1):

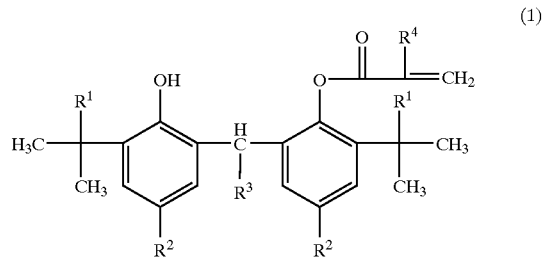

(in the formula, $R^1$ is an alkyl group of 1 to 5 carbon atoms, $R^2$ is an alkyl group of 1 to 5 carbon atoms, $R^3$ is a hydrogen atom or an alkyl group of 1 to 5 carbon atoms, and $R^4$ is a hydrogen atom or a methyl group).

The compound represented by the general formula (1) has a large molecular weight and therefore low volatility at high temperatures and is very high in inhibitory effect for polymerization of adamantyl ester monomer. As a result, the adamantyl ester monomer composition of the present invention containing the compound has high stability. That is, decomposition or polymerization of adamantyl ester monomer in the composition is prevented even during the long-term storage or high-temperature standing of the composition, and there is no distillation of the polymerization inhibitor when the composition has been subjected to distillation. Therefore, when the composition contains various impurities such as metal components, unreacted raw materials remaining in production of adamantyl ester monomer, reaction by-products and the like, an adamantyl ester monomer of high purity can be obtained from such a composition by a simple distillation operation.

Also, in the reaction by-products are contained such impurities as to promote the gelling of adamantyl ester monomer. Even in a composition containing such impurities, the stabilization effect of the composition can be further enhanced by adding thereto, besides the compound of the general formula (1), a sulfur-based antioxidant and/or a phenol type antioxidant.

Although not clear theoretically, it is presumed that in addition to the excellent stabilization effect of the compound represented by the general formula (1), the sulfur-based antioxidant acts as a decomposer for hydroperoxide and decomposes a peroxide contained in adamantyl ester monomer composition and the phenol type antioxidant acts as a capturing agent for peroxy radical, whereby such preferred effects are exhibited.

The present invention lies also in a process for producing a high-purity adamantyl ester monomer, characterized in that the above-mentioned adamantyl ester monomer composition of the present invention is subjected to distillation to obtain a high-purity adamantyl ester monomer.

According to this production process of the present invention, an adamantyl ester monomer of high purity can be obtained stably by a simple operation of subjecting the present composition to distillation.

An investigation by the present inventors revealed that a crude adamantyl ester monomer obtained by esterification of an adamantane derivative having —OH group, —OM group or =R group [M is an alkali metal atom or MgX (X is a halogen atom) and R is a bivalent aliphatic hydrocarbon group] with an unsaturated carboxylic acid compound or a derivative thereof, particularly a (meth)acrylic acid or a derivative thereof, often contains impurities which promotes the gelling of the monomer per se when the crude monomer is subjected to distillation.

Even in such a case, the gelling of the monomer per se can be prevented sufficiently and a monomer of high purity can be obtained by adding, to the crude adamantyl ester monomer, a compound represented by the general formula (1) and, as necessary, the above-mentioned sulfur-based antioxidant and phenol type antioxidant and subjecting the resulting adamantyl ester monomer composition of the present invention to distillation.

According to the present invention, it becomes possible to easily distill and purify an adamantyl ester monomer whose stable distillation and purification has been difficult. By employing the production process of the present invention, it is also possible to easily obtain an adamantyl ester monomer of high purity which is expected to be used as a resist material for semiconductor. It is also possible to store an adamantyl ester monomer stably for a long period.

BEST MODE FOR CARRYING OUT THE INVENTION

The composition of the present invention contains at least an adamantyl ester monomer having at least one polymerizable unsaturated bond in the molecule and a compound represented by the general formula (1).

The adamantyl ester monomer contained in the composition of the present invention is a compound wherein a monovalent organic residue is bonded to a carbon atom of adamantane skeleton via —O—CO— bond. The organic residue has at least one polymerizable unsaturated bond. As the adamantyl ester monomer, there is no particular restriction, and a known compound can be used.

For easiness of the synthesis, there are preferred compounds represented by the following general formula (2):

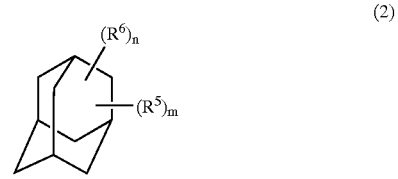

(2)

[in the formula, $R^5$ is a —O—CO—CH=$CH_2$ group or a —O—CO—C($CH_3$)=$CH_2$ group; $R^6$ is an alkyl group of 1 to 6 carbon atoms; m is an integer of 1 to 3; n is an integer of 0 to 4; $R^5$ and $R^6$, two $R^5$s or two $R^6$s may be bonded to a carbon atom of adamantane skeleton].

Of these compounds, particularly preferred are 2-adamantyl (meth)acrylates represented by the following general formula (3):

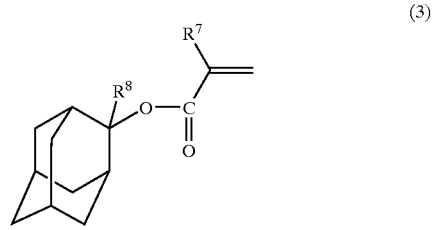

(3)

(in the formula, $R^7$ is a hydrogen atom or a methyl group and $R^8$ is a hydrogen atom or an alkyl group of 1 to 6 carbon atoms), or 1-adamantyl (meth)acrylates represented by the following general formula (4):

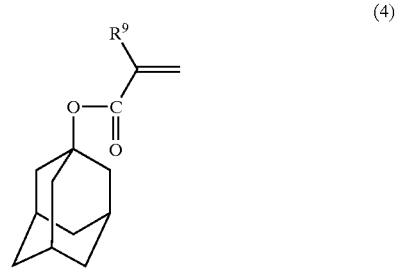

(4)

(in the formula, $R^9$ is a hydrogen atom or a methyl group), because they are useful as a raw material for resist for semiconductor and a very high purity is required As specific examples of the adamantyl ester compound represented by the general formula (3), there are mentioned 2-methyl-2-adamantyl acrylate, 2-ethyl-2-adamantyl acrylate, 2-methyl-2-adamantyl methacrylate, 2-ethyl-2-adamantyl methacrylate, 2-propyl-2-adamantyl acrylate and 2-butyl-2-adamantyl acrylate.

The composition of the present invention contains an adamantyl ester monomer, a compound represented by the general formula (1) and, as necessary, an antioxidant. Owing to the presence of such an antioxidant, the storage stability of the adamantyl ester monomer becomes higher than when no antioxidant is present. Further, when the composition is heated to the boiling point, the compound of the general formula (1) and the antioxidant are not distilled and remain in the composition and a high stabilization effect toward monomer is maintained. Therefore, when the composition is subjected to distillation, decomposition, etc. of adamantyl ester monomer and subsequent gelling and coloring are prevented effectively.

The composition of the present invention contains a compound represented by the general formula (1) as an essential component.

As specific examples of the compound represented by the general formula (1), there are mentioned 2,2'-methylenebis (6-tert-butyl-4-methylphenol) monoacrylate, 2,2'-ethylidenebis(4,6-di-tert-amylphenol) monoacrylate, 2,2'-methylenebis(6-tert-butyl-4-methylphenol) monomethacrylate and 2,2'-methylenebis(6-tert-butyl-4-propylphenol) monoacrylate. These compounds may be used singly or in combination of different kinds.

Of these compounds, particularly preferred is 2,2'-methylenebis(6-tert-butyl-4-methylphenol) monoacrylate which is a compound of the general formula (1) wherein $R^1$ is a methyl group, $R^2$ is a methyl group, $R^3$ is a hydrogen atom and $R^4$ is a hydrogen atom, or 2,2'-ethylidenebis(4,6-di-tert-amylphenol) monoacrylate which is a compound of the general formula (1) wherein $R^1$ is an ethyl group, $R^2$ is a tert-amyl group, $R^3$ is a methyl group and $R^4$ is a hydrogen atom, because they have a high inhibitory effect for polymerization and are easily available.

The use amount of the compound represented by the general formula (1) differs depending upon its kind, the kind of adamantyl ester monomer, and the kinds and amount of the impurities contained. Therefore, a use amount necessary for obtaining a sufficient inhibitory effect for polymerization is determined appropriately, for example, by specifically conducting a preliminary heat stability test for each individual composition. Generally, the use amount of the compound represented by the general formula (1) is preferably 0.01 to 30 parts by mass, particularly preferably 0.1 to 5 parts by mass relative to 100 parts by mass of adamantyl ester monomer.

The composition of the present invention may contain only an adamantyl ester monomer and a compound of the general formula (1). However, the composition preferably contains further a sulfur-based antioxidant and/or a phenol type antioxidant for a higher inhibitory effect for gelling during heating. A composition containing both a sulfur-based antioxidant and a phenol type antioxidant is most preferred.

As to the sulfur-based antioxidant, there is no particular restriction as long as it is a sulfur-containing compound having antioxidancy but having no phenol skeleton. Any known sulfur-containing compound can be used. However, a compound generally used as a sulfur-based secondary antioxidant is preferred from the standpoint of stabilizing effect.

As specific examples of compounds preferably usable as the sulfur-based antioxidant, there are mentioned dialkyl sulfides such as didodecyl sulfide, distearyl sulfide and the like; thiopropionic acid type sulfur compounds such as dilauryl 3,3'-thiodipropionate, dimyristyl 3,3'-thiodipropionate, distearyl 3,3'-thiodipropionate, pentaerythrityl tetrakis(3-laurylthiopropionate), thiobis[2-(1,1-dimethylethyl)-5-methyl-4,1-phenylene]bis[3-(dodecylthio) propionate], thiobis[2-(1,1-dimethylethyl)-5-methyl-4,1-phenylene]bis[3-(dodecylthio)propionate and the like; and thiol group-containing imidazoles such as 2-mercaptobenzimidazole and the like.

Of these, more preferred are thiopropionic acid type sulfur compounds such as pentaerythrityl tetrakis(3-laurylthiopropionate) and the like because they are hardly distilled and show a very high inhibitory effect for gelling.

There is no particular restriction as to the amount of the sulfur-based antioxidant used, but the amount is preferably 10 to 500 parts by mass, particularly preferably 20 to 100 parts by mass relative to 100 parts by mass of the compound represented by the general formula (1) in view of the stabilization (polymerization inhibition) effect of monomer.

As to the phenol type antioxidant, there is no particular restriction as long as it is a phenolic compound having antioxidancy, and a known compound can be used. A compound generally used as a phenolic primary antioxidant is preferably used in view of the stabilization effect.

As specific examples of the compounds preferably used as the phenol type antioxidant, there are mentioned monophenol type compounds such as 2,6-di-tert-butyl-4-methylphenol, 2,6'-di-tert-butyl-4-ethylphenol, butylhydroxyanisole, stearyl β-(3,5-di-tert-butyl-4-hydroxyphenyl)propionate and the like; bisphenol type compounds such as 2,2'-methylenebis(6-tert-butyl-4-methylphenol), 2,2'-methylenebis(6-tert-butyl-4-ethylphenol), 4,4'-butylidenebis(6-tert-butyl-3-methylphenol), 4,4'-thiobis(6-tert-butyl-3-methylphenol), 3,9-bis[2-{3-(3-tert-butyl-4-hydroxy-5-methylphenyl) propionyloxy}-1,1'-dimethylethyl]-2,4,8,10-tetraoxaspiro [5,5]undecane and the like; and phenolic compounds having three or more phenol groups, such as 1,1,3-tris(2-methyl-4-hydroxy-5-tert-butylphenyl)butane, 1,3,5-trimethyl-2,4,6-tris(3,5-di-tert-butyl-4'-hydroxybenzyl)benzene, tetrakis-[methylene-3-(3',5'-di-tert-butyl-4-hydroxyphenyl) propionate]methane, bis[3,3'-bis-(4'-hydroxy-3'-tert-butylphenyl)butyric acid]glycol ester, 1,3,5-tris(3,5-di-tert-butyl-4'-hydroxybenzyl)-S-triazine-2,4,6-(1H,3H,5H)trione and the like.

Of these, particularly preferred are bisphenol type compounds such as 4,4'-thiobis(6-tert-butyl-3-methylphenol) and the like and phenolic compounds having three or more phenol groups, such as tetrakis-[methylene-3-(3',5'-di-tert-butyl-4-hydroxyphenyl propionate)methane and the like because they are hardly distilled and are highly soluble in adamantyl ester monomers.

There is no particular restriction as to the amount of the phenol type antioxidant used, but the amount is preferably 10 to 500 parts by mass, particularly preferably 20 to 100 parts by mass relative to 100 parts by mass of the compound represented by the general formula (1) so that a stabilization effect is exhibited reliably.

The adamantyl ester monomer composition of the present invention may further contain, in addition to the adamantyl ester monomer, the compound represented by the general formula (1) and the antioxidant, a known polymerization inhibitor other than the compound represented by the general formula (1) as long as the advantages of the present invention are not impaired.

The adamantyl ester monomer composition of the present invention may further contain a third component in addition to the adamantyl ester monomer, the compound represented by the general formula (1) and the antioxidant. There is no particular restriction as to the third component, but there are generally mentioned a solvent (e.g. tetrahydrofuran or hexane) used in synthesis of adamantyl ester monomer, unreacted raw materials, reaction by-products, metal components incoming from the environment, etc. These third components differ depending upon the differences in production method, etc. and therefore cannot be specified unconditionally.

However, the impurities contained in a crude product obtained by an ordinary process for production of adamantyl ester monomer, that is, a crude product obtained by as necessary removing a solvent, etc. from the reaction mixture of a synthesis reaction of adamantyl ester monomer, gives no adverse effect in carrying out the present invention. Further, there is no particular restriction as to the content of the third component, but the total amount of the third component is ordinarily 50 parts by mass or less relative to 100 parts by mass of the adamantyl ester monomer.

Incidentally, as a general process for production of adamantyl ester monomer, there is mentioned a process which comprises converting, into an ester, an adamantane derivative having —OH group, —OM group or =R group [M is an alkali metal atom or MgX (X is a halogen atom), and R is a bivalent aliphatic hydrocarbon group], using an unsaturated carboxylic acid compound or a derivative thereof, particularly (meth)acrylic acid or a derivative thereof. Here, the alkali metal atom represented by M is a potassium atom, a sodium atom or the like. The halogen atom represented by X is a chlorine atom, a bromine atom, an iodine atom or the like. The bivalent aliphatic hydrocarbon group represented by R is a methylidene group, an ethylidene group, a propylidene group, an isopropylidene group or the like.

For example, an adamantyl ester monomer represented by the general formula (3) wherein $R^8$ is an alkyl group of 1 to 6 carbon atoms, can be obtained by the following processes (a) to (c).

(a) A process which comprises alkylating 2-adamantanone with a Grignard reagent (e.g. an alkyl magnesium halide) or an organometallic reagent (e.g. an alkyl lithium) to obtain a —OM group-containing adamantane derivative represented by the following general formula (5):

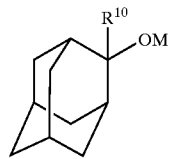

(5)

[in the formula, $R^{10}$ is an alkyl group of 1 to 6 carbon atoms, and M is an alkali metal atom or MgX (X is a halogen atom)] and converting the derivative into a (meth) acrylate using a (meth)acrylic acid halide.

(b) A process which comprises alkylating 2-adamantanone with an organometallic reagent to obtain a 2-alkyl-2-adamantanol (a —OH group-containing adamantane derivative) and converting the compound into a (meth) acrylate using (meth)acrylic acid, (meth)acrylic acid anhydride, a (meth) acrylic acid ester or the like.

(c) A process which comprises alkylating 2-adamantanone with an organometallic reagent, decomposing the resulting metal alkoxide to obtain an alcohol compound, dehydrating the alcohol compound to obtain a 2-alkylideneadamantane (an adamantane derivative having =R group), and subjecting the compound to an addition reaction using (meth)acrylic acid to obtain a (meth)acrylate.

The adamantyl ester monomer represented by the general formula (4) can be obtained, for example, by the following process (d).

(d) A process which comprises converting 1-adamantanol into a (meth)acrylate using (meth)acrylic acid, (meth)acrylic acid anhydride, a (meth)acrylic acid ester or the like.

As to the method for producing the adamantyl ester monomer composition of the present invention, there is no particular restriction and, for example, the following method can be mentioned.

The adamantyl ester monomer composition of the present invention can be obtained, for example, by mixing, into a crude product obtained by a synthesis reaction [one of the above reactions (a) to (d)] for adamantyl ester monomer or a high-purity adamantyl ester monomer obtained by purification of the crude product, the compound of the general formula (1) and, as necessary, the above-mentioned antioxidant.

Here, the crude product includes a reaction mixture after synthesis reaction, a composition obtained by removing a solvent from the reaction mixture by distillation, a composition obtained by treating the reaction mixture with an aqueous basic solution, as necessary washing the resulting mixture, conducting solvent extraction, and further conducting a treatment such as solvent removal by distillation, or the like (hereinafter, each of such compositions may be referred to simply as crude product).

The adamantyl ester monomer composition of the present invention obtained by mixing, into a high-purity adamantyl ester monomer, the compound of the general formula (1) and, as necessary, the above-mentioned antioxidant, is characterized by having high storage stability over a long period.

The adamantyl ester monomer composition obtained by mixing, into the above-mentioned crude product, the compound of the general formula (1) and, as necessary, the above-mentioned antioxidant, has high storage stability.

When the composition is subjected to distillation in order to obtain a high-purity adamantyl ester monomer, there is no coloring of the resulting distillate and gelling of adamantyl ester monomer is prevented. Therefore, distillation of adamantyl ester monomer composition can be conducted stably with no difficulty.

Thus, a high-purity adamantyl ester monomer can be obtained easily by obtaining a crude product by a synthesis reaction for adamantyl ester monomer, such as one of the above-mentioned (a) to (d), mixing thereinto the compound of the general formula (1) and, as necessary, the above-mentioned antioxidant to prepare an adamantyl ester monomer composition of the present invention, and distilling the composition.

The compound of the general formula (1) and the above-mentioned antioxidant added as necessary may be added beforehand to a crude product which is to be distilled, or may be fed, after the start of distillation, into a still, a distillation tower, a distillation tube, a reflux line or the like.

In order to conduct distillation more stably, it is preferred to add, in addition to the compound of the general formula (1), at least either of a sulfur-based antioxidant and a phenol type antioxidant and it is more preferred to add both of them.

There is no particular restriction as to the method of distillation and there can be employed simple distillation or fractional distillation. As a fractionating column used in fractional distillation, there are preferred thin-film type fractionating columns such as vigoureux type, concentric type, rotary band type, packed column type and the like, and plate-shaped fractionating columns such as bubble cap type, perforated plate type and the like. When, in particular, reduced pressure distillation is conducted, a thin-film type fractionating column of low pressure loss is preferred. Also, a known distillation method such as Kugel rohr, thin-film distillation or the like can be employed with no restriction. Further, there is no particular restriction as to the distillation conditions used, such as distillation temperature, distillation pressure, reflux ratio and the like. The distillation conditions are determined appropriately depending upon the boiling point of adamantyl ester monomer, the kinds and amount of the impurities contained, the kinds and use amounts of the compound of the general formula (1) and the antioxidant added as necessary, the purity of adamantyl ester monomer obtained finally, etc. It is generally preferred to conduct distillation at a pressure of 0.01 to 10 mmHg and a still temperature (a composition temperature inside still) of 50 to 150° C.

EXAMPLES

The present invention is described more specifically below by way of Examples and Comparative Examples. However, the present invention is in no way restricted by these Examples.

Incidentally, the symbols used for compounds of the general formula (1) and antioxidants in each Example ad each Comparative Example are shown below in a style of [symbol: compound name].

[Compounds represented by the general formula (1)]
A-1: 2,2'-Methylenebis(6-tert-butyl-4-methylphenol) monoacrylate
A-2: 2,2'-Ethylidenebis(4,6-di-tert-amylphenol) monoacrylate

[Sulfur-Based Antioxidants]
S-1: Distearyl 3,3'-thiodipropionate
S-2: Pentaerythrityl tetrakis(3-laurylthiopropionate)
S-3: Thiobis[2-(1,1-dimethylethyl)-5-methyl-4,1-phenylene] bis[3-(dodecylthio)propionate]
S-4: Distearyl sulfide

[Phenol type antioxidants]
P-1: 2,2'-Methylenebis(6-tert-butyl-4-methylphenol)
P-2: 2,6-Di-tert-butyl-4-methylphenol
P-3: 4,4'-Thiobis(6-tert-butyl-3-methylphenol)
P-4: Tetrakis-[methylene-3-(3',5'-di-tert-butyl-4-hydroxyphenyl)propionate]methane

[Other polymerization inhibitors]
O-1: Methoxyphenol
O-2: Hydroquinone
O-3: Phenothiazine Synthesis Example 1

30 g of 2-adamantanone was dissolved in 100 ml of anhydrous tetrahydrofuran. To the solution was added, at room temperature, 200 ml of a tetrahydrofuran solution containing 1 mole/liter of methyl magnesium bromide, and a reaction was allowed to take place for 3 hours. Then, 5 g of pyridine was added to the reaction mixture and successively 26 g of methacrylic acid chloride was added, followed by stirring at 50° C. for 3 hours.

The reaction mixture was concentrated. Thereto were added 200 ml of hexane and 100 ml of a 1 N aqueous ammonium chloride solution, followed by shaking. The organic phase was separated and then washed with a 5 mass % aqueous sodium hydroxide solution and further with water. The washed organic phase was concentrated to obtain crude 2-methyl-2-adamantyl methacrylate (a crude product) having a purity of 90 mass %.

Synthesis Example 2

200 ml of toluene and 1 g of p-toluenesulfonic acid were added to 70 g of 1-adamantanol and 50 g of methacrylic acid. They were subjected to a reaction with heating and stirring, while water was distilled off using a Dean-Stark trap. The resulting organic phase was washed with water, a 10 mass % aqueous sodium hydrogencarbonate solution and water in this order and distilled to obtain crude 1-adamantyl methacrylate (a crude product) having a purity of 91 mass %.

Comparative Example 1

5 g of the crude product obtained in Synthesis Example 1 was placed in each of two screw-necked test tubes. The test tubes were kept at 120° C. in a constant-temperature oil bath and measured for a time up to gelling of contents (the time is hereinafter may be referred to as gelling time). Incidentally, the gelling time is a time required for the contents of test tube to become non-fluid when the test tube is made upside down. A longer gelling time means superior storage stability, particularly superior stability at high temperatures. The average of the gelling times of the two samples, i.e. the average gelling time was 2.0 hours.

Example 1

5 g of the crude product obtained in Synthesis Example 1 was placed in each of two screw-necked test tubes. Further, 0.01 g of A-1 was placed in each test tube. Then, each test tube was tightly sealed and the contents of each test tube was mixed uniformly to prepare a composition of the present Example.

Next, the two test tubes each containing the above composition of the present Example were kept at 120° C. in a constant-temperature oil bath and determined for average gelling time in the same manner as in Comparative Example 1. The average gelling time was 12.0 hours and was six times that of Comparative Example 1. Thus, the composition of the present Example is improved in high-temperature storage stability.

Example 2

An average gelling time was measured in the same manner as in Example 1 except that A-2 was used as the compound represented by the general formula (1). The average gelling time was 11.5 hours.

Comparative Examples 2 to 8

Average gelling times were measured in the same manner as in Examples 1 and 2 except that the compounds represented by the general formula (1) used in Examples 1 and 2 were changed by various compounds shown in Table 1. The results are shown together in Table 1.

TABLE 1

| | Compound added | Amount added (g) | Average gelling time (hr) |
|---|---|---|---|
| Example 1 | A-1 | 0.01 | 12.0 |
| Example 2 | A-2 | 0.01 | 11.5 |
| Comparative Example 1 | — | — | 2.0 |
| Comparative Example 2 | O-1 | 0.01 | 6.0 |
| Comparative Example 3 | O-2 | 0.01 | 7.0 |
| Comparative Example 4 | O-3 | 0.01 | 7.5 |
| Comparative Example 5 | S-1 | 0.01 | 2.5 |
| Comparative Example 6 | S-2 | 0.01 | 2.5 |
| Comparative Example 7 | P-1 | 0.01 | 3.5 |
| Comparative Example 8 | P-2 | 0.01 | 3.0 |

As shown in Table 1, even when there are used polymerization inhibitors other than compounds represented by the general formula (1), the average gelling times are longer than when there is used no polymerization inhibitor (Comparative Example 1). However, even the longest gelling time is about 65% or less of Examples 1 and 2 and the stabilization effect of that case is lower than that of each Example.

Comparative Example 9

An average gelling time was measured in the same manner as in Comparative Example 1 except that the crude product obtained in Synthesis Example 2 was used. The result is shown in Table 2.

TABLE 2

|  | Compound added | Amount added (g) | Average gelling time (hr) |
|---|---|---|---|
| Example 3 | A-1 | 0.01 | 12.5 |
| Example 4 | A-2 | 0.01 | 11.0 |
| Comparative Example 9 | — | — | 1.5 |
| Comparative Example 10 | O-1 | 0.01 | 6.5 |
| Comparative Example 11 | O-2 | 0.01 | 6.5 |
| Comparative Example 12 | O-3 | 0.01 | 8.0 |
| Comparative Example 13 | S-1 | 0.01 | 2.5 |
| Comparative Example 14 | S-2 | 0.01 | 3.0 |
| Comparative Example 15 | P-1 | 0.01 | 3.0 |
| Comparative Example 16 | P-2 | 0.01 | 3.5 |

Examples 3 and 4

Average gelling times were measured in the same manner as in Example 1 except that 0.01 g of a compound sown in Table 2 was added to 5 g of the crude product obtained in Synthesis Example 2. The results are shown in Table 2.

As shown in Table 2, the average gelling times are 7.3 times or more that of Comparative Example 9. As a result, it is seen that the compositions of the present invention are improved in high-temperature storage stability.

Comparative Examples 10 to 16

Average gelling times were measured in the same manner as in Examples 3 and 4 except that the compounds represented by the general formula (1) used in Examples 3 and 4 were changed by various compounds shown in Table 2. The results are shown together in Table 2.

As shown in Table 2, even when there are used polymerization inhibitors other than compounds represented by the general formula (1), the average gelling times are longer than when there is used no polymerization inhibitor (Comparative Example 2). However, the stabilization effects of such cases are lower than those of Examples 3 and 4.

Example 5

An average gelling time was measured in the same manner as in Example 1 except that 0.01 g of phenothiazine (O-3) was added in addition to A-1 [a compound represented by the general formula (1)]. The results is shown in Table 3.

TABLE 3

|  | Compound added | Amount added (g) | Average gelling time (hr) |
|---|---|---|---|
| Example 5 | A-1 | 0.01 | 14.5 |
|  | O-3 | 0.01 |  |

Examples 6 to 11

Average gelling times were measured in the same manner as in Example 1 except that there were added a compound of general formula (1) and a sulfur-based antioxidant both shown in Table 4. The results are shown in Table 4.

TABLE 4

|  | Compound added | Amount added (g) | Average gelling time (hr) |
|---|---|---|---|
| Example 6 | A-1 | 0.01 | 17.5 |
|  | S-1 | 0.01 |  |
| Example 7 | A-2 | 0.01 | 19.5 |
|  | S-2 | 0.02 |  |
| Example 8 | A-1 | 0.01 | 18.5 |
|  | S-1 | 0.04 |  |
| Example 9 | A-2 | 0.001 | 17.5 |
|  | S-2 | 0.02 |  |
| Example 10 | A-1 | 0.01 | 19.0 |
|  | S-3 | 0.02 |  |
| Example 11 | A-2 | 0.01 | 18.5 |
|  | S-4 | 0.04 |  |

It is seen from Table 4 that the stabilization effect of adamantyl ester monomer composition is improved by a combination use of a compound represented by the general formula (1) and a sulfur-based antioxidant.

Also, as is clear from the comparison of Table 3 and Table 4, a combination use of a compound represented by the general formula (1) and a sulfur-based antioxidant gives a higher stabilization effect than a combination use of the compound and an amine type polymerization inhibitor.

Examples 12 to 16

Average gelling times were measured in the same manner as in Example 1 except that, as shown in Table 5, there was added a mixture of a compound represented by the general formula (1), a sulfur-based antioxidant and a phenol type antioxidant. The results are shown in Table 5.

TABLE 5

|  | Compound added | Amount added (g) | Average gelling time (hr) |
|---|---|---|---|
| Example 12 | A-1 | 0.01 | 26.5 |
|  | S-2 | 0.02 |  |
|  | P-3 | 0.01 |  |
| Example 13 | A-1 | 0.01 | 24.5 |
|  | S-2 | 0.02 |  |
|  | P-4 | 0.01 |  |
| Example 14 | A-1 | 0.01 | 21.5 |
|  | S-2 | 0.02 |  |
|  | P-1 | 0.01 |  |
| Example 15 | A-2 | 0.01 | 23.0 |
|  | S-2 | 0.02 |  |
|  | P-1 | 0.01 |  |
| Example 16 | A-2 | 0.01 | 26.0 |
|  | S-1 | 0.02 |  |
|  | P-4 | 0.01 |  |

It is seen from Table 5 that a combination use of a compound represented by the general formula (1), a sulfur-based antioxidant and a phenol type antioxidant gives a further improved stabilization effect than a combination use of the former two substances.

Example 17

0.18 g of A-2, a compound of general formula (1) was added to 60 g of the crude product obtained in Synthesis Example 1. The resulting composition was subjected to reduced pressure distillation.

The reduced pressure distillation was conducted at a vacuum of 0.3 mmHg using a 5-cm vigoureux type fractionating column and a total condensation type reflux fractionator while air was introduced into the composition through a glass capillary. The distillation was conducted while the distillate was subjected to compositional analysis using a gas chromatograph. The initial distillate was cut and the collection of the main distillate was begun when the purity of 2-methyl-2-adamantyl methacrylate in distillate exceeded 80%. By collecting the main distillate (a fraction of 80 to 115° C.), 2-methyl-2-adamantyl methacrylate could be obtained at a purity of 95.2 mass % (distillation yield: 81%).

11 Hours were taken for the distillation. However, no gel was formed in the still, the pipe, etc. The main distillate was almost colorless and the A-2 content in the main distillate was the detection limit or less (50 ppm or less).

Example 18

Reduced pressure distillation was conducted in the same manner as in Example 17 except that the amount of the crude product was changed to 100 g and 0.3 g of A-1 and 0.6 g of S-1 were added thereto. By collecting the main distillate, 2-methyl-2-adamantyl methacrylate could be obtained at a purity of 95.6 mass % (distillation yield: 77%). 15 Hours were taken for the distillation. However, no gel was formed in the still, the pipe, etc. The main distillate was almost colorless and the A-1 content in the main distillate was the detection limit or less (50 ppm or less).

Example 19

Reduced pressure distillation was conducted in the same manner as in Example 17 except that there were added, to 200 g of the crude product, 0.6 g of A-1, 1.2 g of S-2 and 0.6 g of P-3. By collecting a main distillate, 2-methyl-2-adamantyl methacrylate could be obtained at a purity of 95.3 mass % (distillation yield: 80%). 24 Hours were taken for the distillation. However, no gel was formed in the still, the pipe, etc. The main distillate was almost colorless and the A-1 content in the main distillate was the detection limit or less (50 ppm or less).

Comparative Example 17

The crude product obtained in Synthesis Example 1 was subjected to distillation in the same manner as in Example 17, with no addition of a compound of general formula (1), an antioxidant, or the like.

The initial distillate was cut and collection of the main distillate was begun when the purity of 2-methyl-2-adamantyl methacrylate exceeded 80%. However, gel was gradually formed in the still and, after 4 hours from the start of distillation, there was no distillation of the main distillate. The distillation yield of the main distillate was only 13%.

Comparative Example 18

Distillation was conducted in the same manner as in Example 17 except that 0.18 g of 0-3 alone was added in addition to A-2, a compound of the general formula (1). The initial distillate was cut and collection of the main distillate was begun when the purity of 2-methyl-2-adamantyl methacrylate exceeded 80%. However, gel was gradually formed in the still and, after 10 hours from the start of distillation, there was no distillation of the main distillate. The distillation yield of the main distillate was 63%. The main distillate had a light green color and contained 660 ppm of phenothiazine.

What is claimed is:

1. An adamantyl ester monomer composition characterized by containing at least an adamantyl ester monomer wherein a carbon atom of the adamantane skeleton is bonded with an organic group having at least one polymerizable unsaturated bond via a —C(=O)— group, and a compound represented by the following general formula (1):

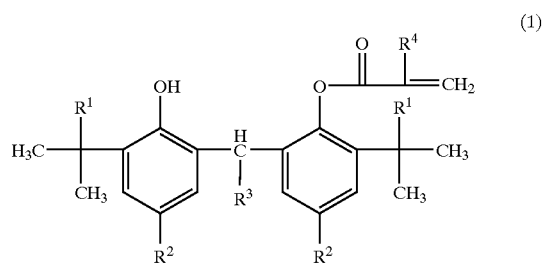

in (the formula, $R^1$ is an alkyl group of 1 to 5 carbon atoms, $R^2$ is an alkyl group of 1 to 5 carbon atoms, $R^3$ is a hydrogen atom or an alkyl group of 1 to 5 carbon atoms, and $R^4$ is a hydrogen atom or a methyl group.

2. An adamantyl ester monomer composition according to claim 1, further containing a sulfur-based antioxidant.

3. An adamantyl ester monomer composition according to claim 2, further containing a phenol type antioxidant.

4. An adamantyl ester monomer composition according to claim 1, wherein the adamantly ester monomer is represented by the formula (3):

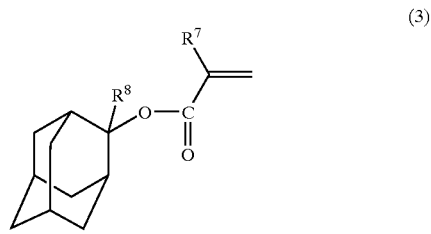

wherein $R^7$ is a hydrogen atom or a methyl group; and $R^8$ is a hydrogen atom or an alkyl group of 1 to 6 carbon atoms.

5. An adamantyl ester monomer composition according to claim 1, wherein the adamantly ester monomer is represented by the formula (4):

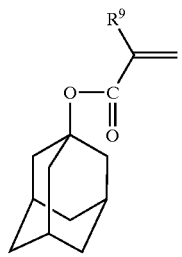

(4)

wherein $R^9$ is a hydrogen atom or a methyl group.

6. An adamantyl ester monomer composition according to claim 1, wherein the organic group residue having at least one polymerizable unsaturated and bonded to the carbon atom of the adamantane skeleton via a —C(=O)— group is an acrylate group.

7. An adamantyl ester monomer composition according to claim 1, wherein the adamantly eater monomer is 2-methyl-adamantyl acrylate, 2-ethyl-2-adamantyl acrylate, 2-methyl-2-adamantyl methacrylate, 2-ethyl-2-adamantyl methacrylate, 2-propyl-2-adamantyl acrylate or 2-butyl-2-adamantyl acrylate.

8. An adamantyl ester monomer composition according to claim 1, wherein $R^1$ is a methyl group, $R^2$ is a methyl group, $R^3$ is a hydrogen atom and $R^4$ is a hydrogen atom.

9. An adamantyl ester monomer composition according to claim 1, wherein $R^1$ is an ethyl group, $R^2$ is a tert-amyl group, $R^3$ is a methyl group and $R^4$ is a hydrogen atom.

10. An adamantyl eater monomer composition according to claim 1, wherein the amount of the compound represented by formula (1) is 0.01 to 30 parts by mass relative to 100 parts by mass of the adamantyl ester monomer.

11. An adamantyl ester monomer composition according to claim 1, wherein the amount of the compound represented by formula (1) is 0.1 to 5 parts by mass relative to 100 parts by mass of the adamantyl ester monomer.

12. A process for distillation to obtain an adamantyl ester monomer, comprising subjecting the adamantyl ester monomer composition according to claim 1 to distillation to obtain an adamantyl ester monomer.

13. A process for distillation to obtain an adamantyl ester monomer, comprising subjecting the adamantyl ester monomer composition according to claim 2 to distillation to obtain an adamantyl eater monomer.

14. A process for distillation to obtain an adamantyl ester monomer, comprising subjecting the adamantyl eater monomer composition according to claim 3 to distillation to obtain an adamantyl eater monomer.

15. A process for distillation to obtain an adamantyl ester monomer, comprising subjecting the adamantyl ester monomer composition according to claim 4 to distillation to obtain an adamantyl ester monomer.

16. A process for distillation to obtain an adamantyl ester monomer, comprising subjecting the adamantyl ester monomer composition according to claim 5 to distillation to obtain an adamantyl ester monomer.

17. A process for distillation to obtain an adamantyl ester monomer, comprising subjecting the adamantyl ester monomer composition according to claim 6 to distillation to obtain an adamantyl ester monomer.

18. A process for distillation to obtain an adamantyl ester monomer, comprising subjecting the adamantyl ester monomer composition according to claim 7 to distillation to obtain an adamantyl ester monomer.

19. A process for distillation to obtain an adamantyl ester monomer, comprising subjecting the adamantyl ester monomer composition according to claim 8 to distillation to obtain an adamantyl ester monomer.

20. A process for distillation to obtain an adamantyl ester monomer, comprising subjecting the adamantyl ester monomer composition according to claim 9 to distillation to obtain an adamantyl ester monomer.

21. A process for distillation to obtain an adamantyl ester monomer, comprising subjecting the adamantyl ester monomer composition according to claim 10 to distillation to obtain an adamantyl ester monomer.

* * * * *